United States Patent [19]

Orthwein

[11] 4,059,900
[45] Nov. 29, 1977

[54] CLIP-ON DENTAL RESTORATION AND TOOLS FOR REMOVING SAME

[76] Inventor: William C. Orthwein, P.O. Box 3332, Carbondale, Ill. 62901

[21] Appl. No.: 746,193

[22] Filed: Nov. 30, 1976

Related U.S. Application Data

[63] Continuation-in-part of Ser. No. 613,196, Sept. 15, 1975, abandoned.

[51] Int. Cl.$^2$ .............................................. A61C 13/22
[52] U.S. Cl. ........................................................... 32/5
[58] Field of Search ..................................... 32/5, 6, 8

[56] References Cited

U.S. PATENT DOCUMENTS 1,436,016  11/1922  Nese ........................................... 32/8

*Primary Examiner*—Robert Peshock
*Attorney, Agent, or Firm*—Beall & Jeffery

[57] ABSTRACT

The invention relates to a removable dental restoration for filling an edentulous space defined at each end by a natural tooth, the restoration having at each end a means for resiliently gripping the adjacent natural tooth. In a first embodiment, the gripping means is releasable by application of opposing forces to the longitudinal side walls of the restoration. A second embodiment has the gripping means releasable by applying a simultaneous force to the end wall of each respective gripping means. Further embodiments also have gripping means releasable by application of opposing forces to the longitudinal side walls of the restoration, but the gripping means are formed separately from and attachable to the restoration. A plier-type tool is provided for removing the first type of restoration, wherein the plier jaws have a rigid convex central portion surrounded by resiliently compressable locating fingers. The locating fingers permit the jaws to be located at the proper position on the restoration at which time closing of the jaws causes the convex central portions of the jaws to press against the longitudinal walls of the restoration, thereby releasing the gripping means. A tool is provided for removing the second type of restoration by applying forces to simultaneously release the gripping means at each end of the restoration.

15 Claims, 18 Drawing Figures 4,059,900

CLIP-ON DENTAL RESTORATION AND TOOLS FOR REMOVING SAME

This application is a continuation in-part of application Ser. No. 613,196, filed Sept. 15, 1975 and now abandoned.

BACKGROUND OF THE INVENTION

THE PRIOR ART

Many types of restorations are known in the art which employ clamps, clasps, and the like for gripping adjacent teeth by the temporary bridge tooth. However, the clamp is ordinarily cemented or otherwise fastened to the side of the false tooth and therefore is not easily releasable. For example, U.S. Pat. No. 3,047,952 discloses a clasp for removable false teeth which is only partially embedded in the false tooth. While this type of clasp does effectively hold the restoration in place for most purposes, it may not have sufficient gripping force to hole the restoration during vigorous mastication of chewy or tough foods. Should the clasp be made with sufficient gripping forces to hold the restoration in place during such mastication, it may be difficult to remove for cleaning and would not be easily replaced.

Other types of removable bridges are also known in which the gripping means are releasable by moving a lever which protrudes from the outside surface of the restoration. For example, French Pat. No. 780,623 discloses a bridge which is split vertically so that it may be removed by sliding a release lever. This type of restoration has the disadvantage of moving parts and blind holes which may break down or collect foreign particles. The restoration may be difficult to keep clean.

U.S. Pat. No. 2,722,052 shows the use of a metallic base having clasps for gripping the adjacent teeth and having openings for receiving porcelain or other artificial teeth. This type of restoration may have some of the drawbacks associated with the restoration disclosed in U.S. Pat. No. 2,047,952, as discussed above.

There is a clear need in the art for a dental restoration which will firmly grasp the natural teeth adjacent to an edentulous space in the mouth, yet be easily releasable for removal and cleaning without having blind holes or moving parts to break down or collect food particles.

SUMMARY OF THE INVENTION

The present invention comprises a removable dental restoration for filling an edentulous space in the mouth defined at each side by a natural tooth. The restoration has releasable gripping means for engaging the adjacent natural teeth. In a first embodiment, a single restoration is provided and the gripping means is releasable by applying side pressure to the resilient longitudinal walls of the restoration. A plier-like tool is provided for applying such pressure at the proper location. A second embodiment of the present invention includes a series of restorations and has the gripping means releasable by applying pressure to a single wall of the gripping means at each end of the restoration. A tool is also provided for application of pressure at the correct points for removal of the latter type of restoration. Further embodiments have gripping means which are formed separately from the restoration, but attached thereto.

The principal objective of the present invention is to provide a removable dental restoration which may comprise a single restoration or a series of restorations and which, in either form, are firmly and resiliently clamped in place and which can be quickly and easily removed for cleaning purposes.

BRIEF DESCRIPTION OF THE APPLICATION DRAWINGS

DETAILED DESCRIPTION OF THE PREFERRED EMBODIMENTS

Figure 1:
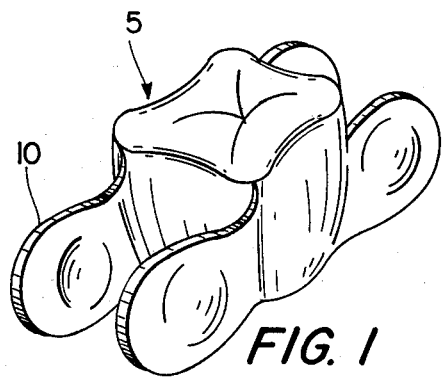
FIG. 1 is a perspective view of a first embodiment of the present invention.
Figure 2:
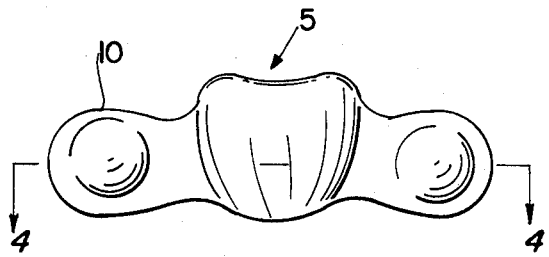
FIG. 2 is a front elevational view of the restoration of FIG. 1.
Figure 3:
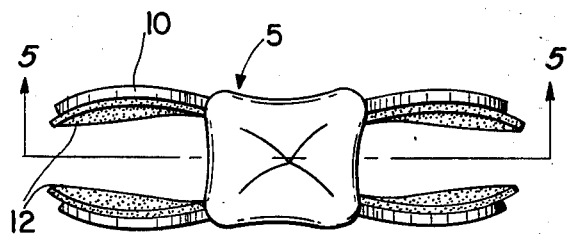
FIG. 3 is a top plan view of the restoration of FIGS. 1 and 2.
Figure 4:
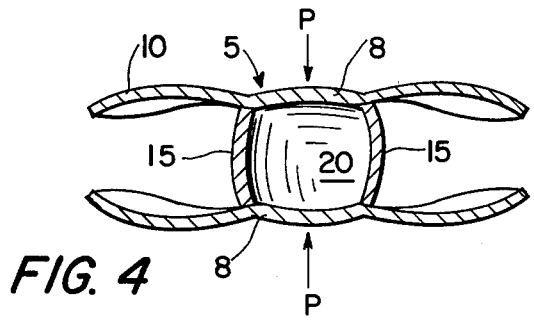
FIG. 4 is a cross-sectional view taken along line 4—4 of FIG. 2.

Referring initially to the form of the invention illustrated in FIGS. 1-9 of the drawings. FIG. 1 is a perspective view of the dental restoration, which includes a central body portion 5 shaped to simulate a natural tooth and gripping means 10 at each end for at least partially encircling and grasping natural teeth at both sides of the restoration. As can be seen in FIGS. 2 and 3, the gripping means are formed to complement the contour of the adjacent teeth to be gripped in order to provide a more secure fastening of the restoration in the mouth. As shown in FIG. 4, longitudinal walls 8 and end walls 15 form the central body portion of the restoration which has a hollow central area 20. The gripping means comprise gripping arms 10 at each end of the body portion which are preferably integrally formed with the longitudinal walls 8. The longitudinal walls and gripping arms are formed from a resilient material, such as spring metal, and the end walls 15 can likewise be formed of metal and are relatively rigid so as to provide the desired firmness of rigidity to the restoration. The end walls 15 may be separately formed as shown in FIG. 4 and secured to the longitudinal walls 8 to form the body portion.

To install the restoration, inwardly directed pressure is applied to the longitudinal walls 8 of the body portion, which causes the walls to flex inwardly and, because of the fulcrum effect of the rigid end walls 15, the gripping arms 10 are caused to spread apart. Releasing the pressure against the resilient, longitudinal walls 8 will permit the longitudinal walls to flex outwardly to their original position, thus causing the gripping arms 10 to close. Cushions of nylon, or other relatively soft material, may optionally be inserted between the gripping arms and the natural teeth being gripped so that the holding forces may be uniformly distributed over the natural teeth. This cushion material should be inert relative to the chemicals in the mouth and the foods eaten. Such a cushion material is shown attached to the gripping surfaces of gripping arms 10 at the left portion of FIG. 3.

Figure 5:
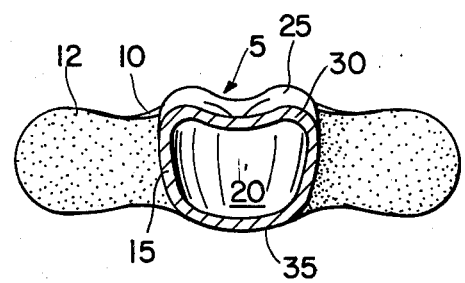
FIG. 5 is a cross-sectional view taken along line 5—5 of FIG. 3.

Referring to FIG. 5, the central body portion of the restoration further includes lower and upper walls 30 and 35, respectively, which, along with longitudinal walls 8 and end walls 15, define the hollow central area 20. In FIG. 5, the central body portion is shown having a crown 25 superimposed on the upper wall 35 to simulate a natural tooth. This crown may be of porcelain, acrylic or other materials known in the art. The central body portion and gripping means are preferably constructed of relatively inert metals, such as stainless steel and gold, although it is to be understood that synthetic materials could also be employed if they possess the necessary characteristics. While the restoration of FIGS. 1-9 is shown with a central body portion having substantially flat walls, it is to be noted that the walls may be curved so that the central body portion defines a cylincrical, triaxial ellipsoidal, prolate spheroidal, oblate spheroidal or spherical form.

Figure 6:
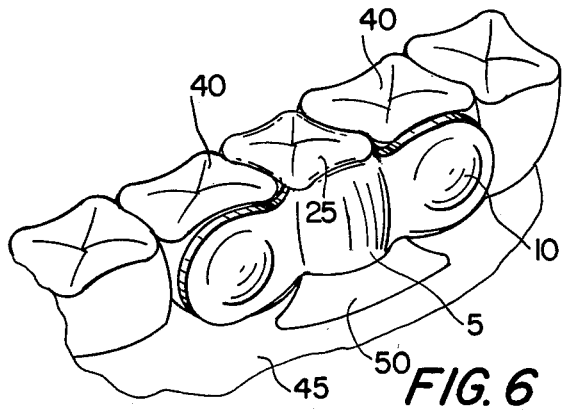
FIG. 6 illustrates the dental restoration of FIG. 1 with an attached base portion and shown in position between the natural teeth which define an edentulous space.
Figure 7:
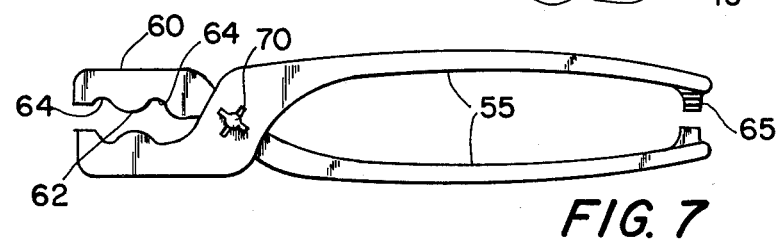
FIG. 7 is a top plan view of a tool for releasing the gripping means of the tool of FIGS. 7 and 8 with locating fingers in place and engaging the longitudinal wall of the dental restoration.
Figure 8:
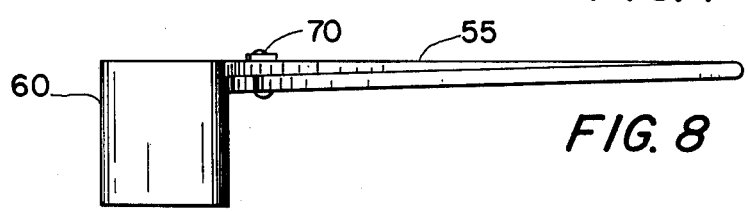

In FIG. 6, the restoration is shown in place in an edentulous space in the mouth defined by adjacent natural teeth commonly indicated at 40 and natural gum 45. The restoration is provided with a base 50, preferably of flesh-colored material such as arcylic. The base is cast to fit the contour of the gum and ridge of the edentulous space and serves to provide support and lend a more pleasing appearance. Furher support for the restoration may be obtained from brackets resting on the adjacent teeth.

Figure 9:
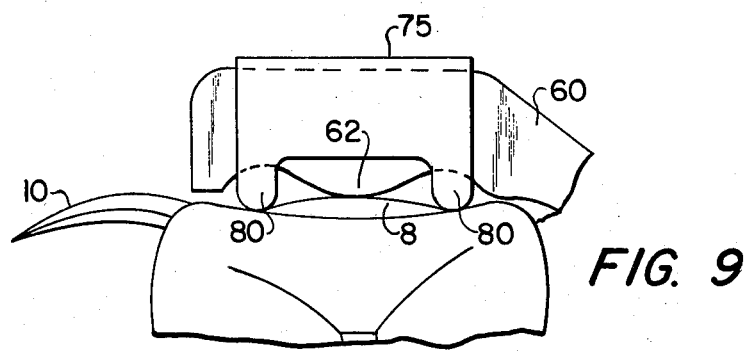
FIG. 9 is a view of the tool of FIGS. 7 and 8 having a resiliently compressible glove over the jaw face.
Figure 10:
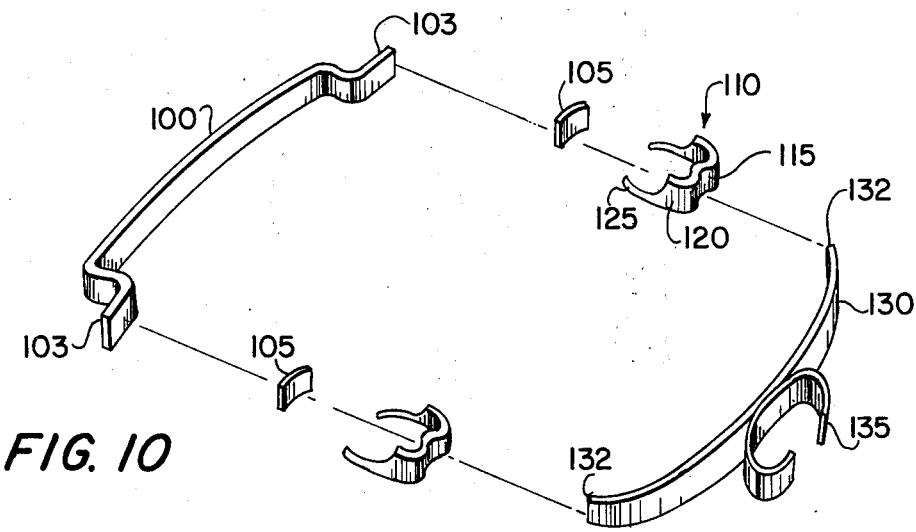
FIG. 10 is an exploded view of a second embodiment of the present invention.

Although the longitudinal walls may be constructed of weak enough spring material that the restoration may be removed by finger forces, it is preferable to have more gripping force than such springs would provide. A tool for removing the dental restoration of FIGS. 1-6 is accordingly shown in FIGS. 7 and 8. The tool generally resembles a pliers and includes a pair of handles 55 which are pivotally interconnected by a pin 70. The pin 70 is formed integrally with one of the handles 55. Each handle has at the gripped end a small stop 65, the stops being in opposing positions on the handles so that full closure of the jaws is not permitted. In addition, pin 70 is keyed so that the jaw handles may be separated for cleaning. Each handle is formed at its opposite end with a gripping jaw 60 shaped to include a rigid central convex portion 62 defined by adjacent channels 64. In FIG. 9 the jaw face shown is provided with a resiliently compressible glove 75 having locating fingers 80 extending into the channels 64. The locating fingers so extend beyond the apex of the convex central portion 62 of the jaw face that when the jaws are arranged around a restoration as shown in FIG. 9, the locating fingers will aid in positioning the jaw faces so that the convex portions 62 of the jaws will contact the central body portion of the restoration at the mid point of the longitudinal walls 8. Closing the jaws slightly will flex the longitudinal walls inwardly; thereby releasing the gripping arms 10, as above described. Stops 65 are provided to prevent excess pressure on the longitudinal walls. The pliers may be of any conventional rigid material such as metal or a rigid synthetic material, while the glove and locating fingers are preferably constructed from a soft plastic material.

The dental restoration of the first embodiment may have the central body portion shaped to simulate a natural tooth or may be made smaller than the edentulous space to be filled and embedded in a material which simulates a natural tooth. As noted above, a crown 25 may be fastened to the upper wall 35 of the central body portion. A flexible coating such as nylon might also be applied to the gripping means and longitudinal walls to simulate the natural tooth coloring.

Figure 11:
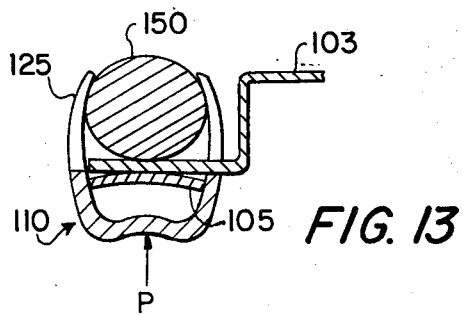
FIG. 11 shows the restoration of FIG. 11 assembled and having a lower base portion.
Figure 12:
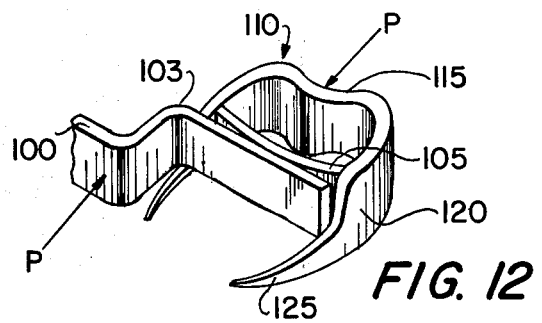
FIG. 12 is a detailed showing of the spring segment and gripping means of the embodiment of FIG. 10.
Figure 13:
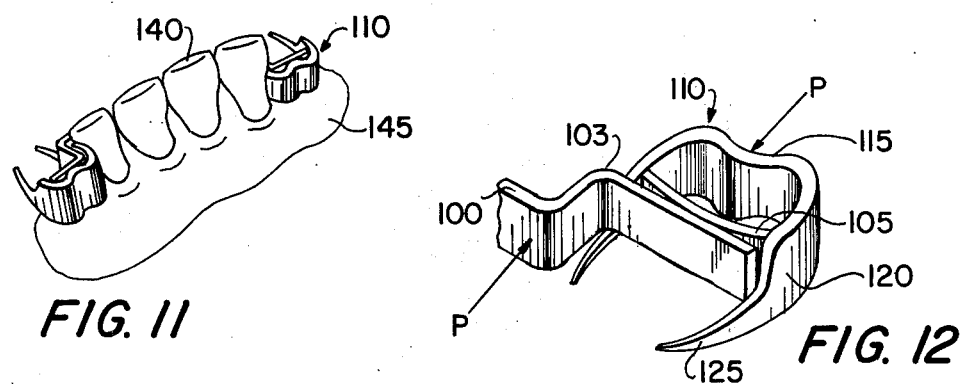
FIGS. 13 and 14 illustrate how the embodiment of FIG. 10 grips an adjacent natural tooth.
Figure 14:
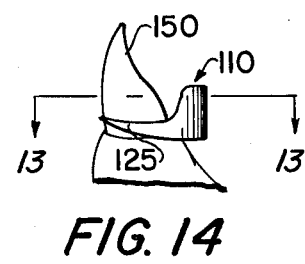

Reference is now made to the form of the invention illustrated in FIGS. 10-14. The restoration in this form is designed to fill an edentulous space having a length equal to several missing teeth, with the space being defined at each side by a natural tooth and having a ridge along the gum. A rigid bar 100 is shaped to follow the curve of the natural ridge and has offset sections 103 at each end which extend partially around the natural tooth to be gripped. Spring segments 105 are fastened to the offset sections 103 as shown in FIG. 12 by soldering or other means. A gripping means 110 is provided at each end of the restoration for engaging the spring segment 105 and the adjacent tooth to be gripped. Each gripping means is generally U-shaped and has an end wall 115, side walls 120 extending perpendicularly to the end wall and spaced apart for engaging the spring segment, and prongs 125 extending from each side wall for gripping the natural tooth. Side walls 120 of the gripping means 110 are slanted sufficiently so that when spring segment 105 is pressed toward end wall 115, the side walls spread apart, releasing the gripping effect of prongs 125. The prongs 125 are small enough to fit the spaces between natural teeth at the gun line. Application of directional forces P to the ends of restoration, as shown in FIG. 12 at one end of the restoration, will cause the prongs 125 to disengage a natural tooth 150 being gripped, as shown in FIG. 13.

The rigid bar 100 supports a series of artificial teeth 140, as shown in FIG. 11, with the bar being artificial teeth 140, as shown in FIG. 11, with the bar being preferably embedded in the artificial teeth. A base portion 145 cast to fit the contour of the gum simulates the natural gum and provides vertical support for the restoration. The artificial teeth 140 and base portion 145 may be of any suitable material, such as acrylic.

A special tool is provided for applying the appropriate forces for removal of the restoration shown in FIG. 11 from the mouth of the wearer. The tool consists of a curved removal bar 130 having tips 132 protruding at an angle to the longitudinal axis of the bar and being spaced sufficiently apart for simultaneously contacting the end walls 115 of the gripping means 110, as can be seen from the exploded, FIG. 10 view. A finger clip 135 is provided so that the user may insert the index finger into the finger clip and apply the tool to the gripping means. By manually pressing the removal bar toward the rigid bar 110, the prongs 125 will be disengaged and the restoration may be easily lifted from the mouth for cleaning. It will be noted that the gripping means 110 protrudes inwardly into the mouth when the restoration is in place. However, such protrusion is not sufficient to cause discomfiture to the wearer.

Figure 15:
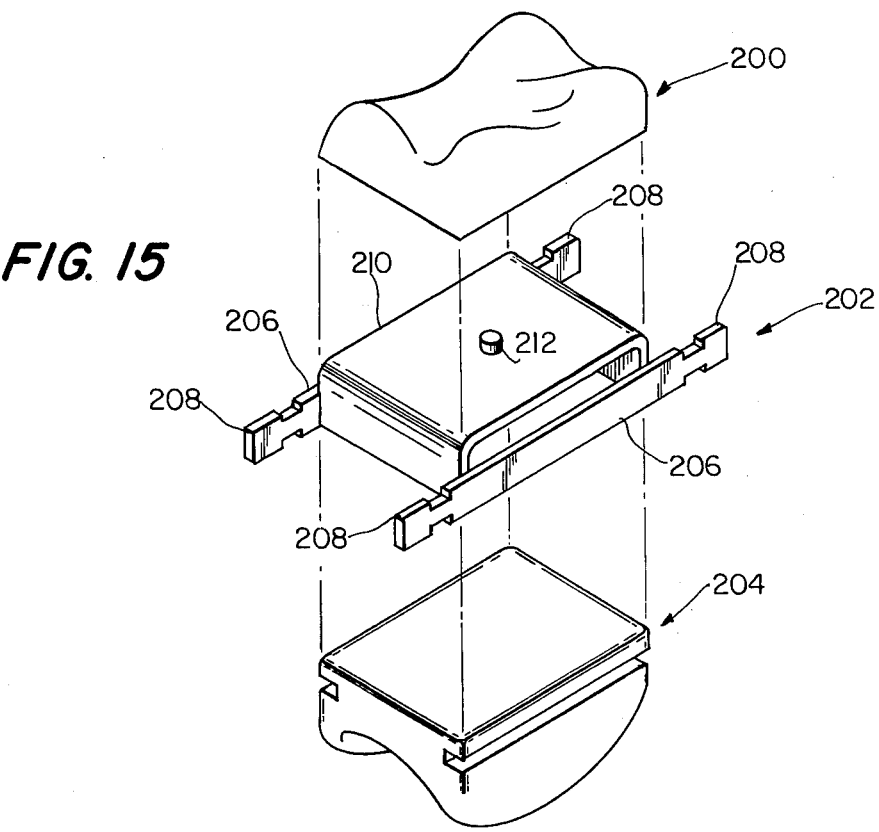
FIG. 15 is an exploded perspective view of a further embodiment of the invention.

FIG. 15 shows an exploded perspective view of a further embodiment of the present invention. The dental restoration shown in FIG. 15 comprises three parts; a crown 200, a spring base 202, and a resilient filler 204. The FIG. 15 embodiment is intended to provide a lower profile restoration than that of the FIG. 1 embodiment, when such is necessary to match the lower profile of teeth for some individuals.

The spring base comprises two longitudinal side walls 206, each having a clip means 208 at its ends for receiving a clip extension which grips the adjacent teeth. The longitudinal end walls 206 are attached, by welding or other suitable means, to an inverted, rigid channel member 210, as shown in FIG. 15. Attached to the upper wall of the channel member 210 is a stud 212 for recieving a corresponding recess (not shown) in the lower surface of the crown member 200.

Although a single stud 212 is shown for mechanical attachment of the crown to the spring base member 202, other arrangements of lugs and/or studs could alternatively be employed. The stud may be deleted is an adhesive of a suitable type is used to bond the crown to the spring base. The longitudinal walls 206 of spring base 202 are preferably constructed of a resilient material having an inert outer surface such as coated spring metal, and the inverted channel member and lug 212 may be constructed of the same material, if desired. The inverted U-shaped channel member must be sufficiently rigid to provide a fulcrum for flexing of the longitudinal side walls 206 at each point where the channel member is joined with a longitudinal side wall. Channel member 210 should, however, be somewhat resilient so as to avoid breaking of the weld with th longitudinal side walls 206 when such side walls are flexed.

The crown member 200 may be constructed of any suitable material, such as porecelain, acrylic or other materials known in the dental art. The shape of crown member 200 will be dictated by the contour and profile of adjacent teeth. It is preferred that a suitable adhesive be placed between the crown and the spring base to secure these members to one another, although a tight friction fit of these members may suffice.

Located beneath the spring base 202 is a resilient filler 204, formed of a relatively soft material. Biting forces are transmitted to the jaw through the plastic filler and aid in retarding contraction of bone and tissue at the site of the restoration. The filler may also relieve some load from th clips which grip adjacent teeth. Filler 204 is shown molded so as to fill any external openings of the spring base member, thereby avoiding any openings in the assembled restoration which would trap food particles.

The resilient filler is preferably of a synthetic, plastic material having a typical hardness about equal to that of a common lead pencil eraser. A typical range of hardness for the plastic filler may be, for example 15–75 Shore A, although the specific hardness of the filler for a particular restoration must be selected for individual satisafaction of the restoration wearer.

Figure 16:
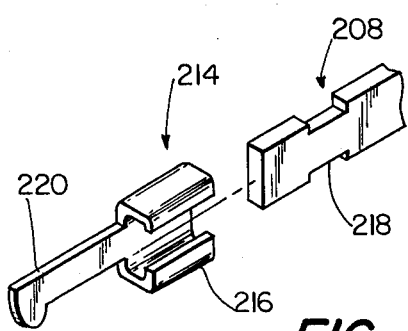
FIG. 16 shows a clip extension which attaches to the spring base of the FIG. 15 restoration for gripping adjacent teeth.

FIG. 16 shows in the righthand portion one of the spring clips 208 of spring base member 202. The spring clip 208 is designed to receive a clip extension 214 which has lugs 216 for engaging the recessed portions 218 clip 208. A gripping arm 220 is provided on the clip extension 214 and is custom made to firmly grip the adjacent teeth. It will be understood that each of the spring clips 208 of base member 202 will be fitted with a clip extension 214.

The restoration of FIG. 15 is then installed in the wearer's mouth in the same fashion as the restoration of FIG. 1. A plier-like tool of similar device is used to depress the center portions of longitudinal arms 206 of the spring base member 202, thereby causing the gripping arms 220 to be spread apart. The restoration is located in the mouth and released, thereby causing the gripping arms to firmly hold the restoration thereby causing the gripping arms to firmly hold the restoration in place.

Figure 17:
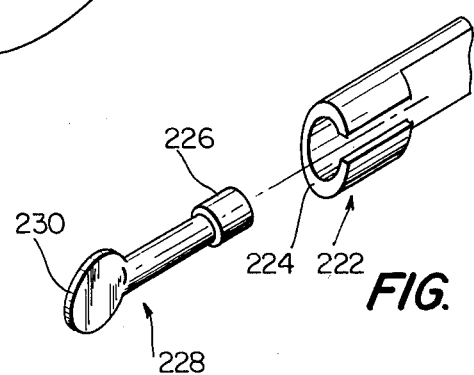
FIGS. 17 and 18 show further forms of the clip extension for gripping teeth adjacent to the restoration.
Figure 18:
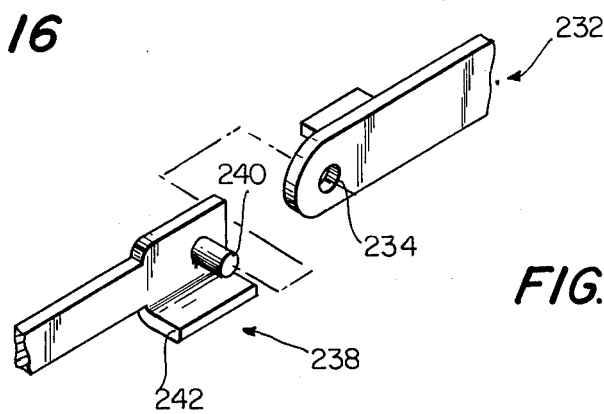

Variations of the spring clip and clip extension members 208 and 214, respectively, are shown in FIGS. 17 and 18. In FIG. 17, the spring clip is modified as shown at 222, so as to form a substantially circular opening 224 which receives and firmly holds end 226 of clip extension 228. Note that the gripping arm 230 of FIG. 17 may be shaped as shown to cover a larger area of the adjacent tooth which is gripped. FIG. 18 shows yet another embodiment of the spring clip and clip extension joining means, wherein spring clip 232 has an opening 234 transverse to the spring clip axis, and also has a tab 236 adjacent thereto. The corresponding clip extension 238 has a complementary configuration with a stud 240 and tab 242, as shown. The tabs provide frictional engagement of the parts.

It will be understood that the spring clip and clip extension combinations shown in FIGS. 16—18 are not intended to exclude other possible means of mating the clip extensions to the spring base. It is also to be noted that the concept of using separately formed clip extension which meet with spring clips on the restoration may be employed with the restoration of FIG. 1. In such case, gripping arms 10 of FIG. 1 would be shortened and formed to receive a mating clip extension. The advantage of this is that only a limited variety of base member sizes need be maintained in stock at the dental laboratory, yet custom-made clip extensions may be fitted to a stock size base member to accomodate the particular tooth size, shape and position, of the restoration user.

The resilient filler member 204 shown in FIG. 15 is also preferably molded to a custom fit to the ridge and tissue defining the edentulous space. However, the filler member is optional and, if the gripping arms are adequately fitted and provide a tight enough grip, the filler member may be deleted.

It will be understood by those skilled in the art that various modifications of the present invention are possible without, however, departing from the spirit and scope of the present invention as defined by the appended claims.

I claim:

1. A removable dental restoration for filling an edentulous space defined at least at one end by a natural tooth, comprising a central body portion shaped to simulate a natural tooth, said central body portion comprising a pair of substantially parallel resilient longitudinal walls, a pair of substantially rigid end walls substantially perpendicular to said longitudinal walls, an upper wall and a lower wall; and gripping means extending from each said longitudinal wall for at least partially encircling and releasably gripping an adjacent natural tooth, whereby said gripping means resiliently clamps said restoration and can be released by applying pressure inwardly against said longitudinal walls, said substantially rigid end walls serving as fulcrum points about which said gripping means pivot for movement away from gripping engagement with said adjacent natural tooth when such inward pressure is applied.

2. The dental restoration of claim 1, further comprising a base member attached to the lower wall and formed to rest upon the ridge and tissue between the natural teeth which defines the edentulous space to be filled.

3. The dental restoration of claim 1, wherein said central body portion is smaller than the edentulous space to be filled and is embedded in an inert material shaped to simulate at least one natural tooth, said inert material comprising a rigid crown attached to the upper wall of said central body portion and a flexible coating applied to said longitudinal walls.

4. The dental restoration of claim 1, wherein each said gripping means is integrally formed with the corresponding longitudinal wall.

5. The dental restoration of claim 1, wherein each said longituidinal wall includes for receiving a corresponding gripping means, and said gripping means includes means for mating with said receiving means, whereby each said gripping means is firmly retained on a longitudinal wall.

6. A removable dental restoration for filling an edentulous space defined at each end by an adjacent natural tooth and having an underlying ridge, comprising a rigid bar carrying at least one restoration, said bar being curved to follow said ridge of the edentulous space and having at each end an offset section extending at least partially around said adjacent natural tooth; a spring segment attached to each of said offset section; and gripping means at each end of said bar for simultaneously engaging said spring segment and said adjacent natural tooth, said gripping means comprising a resilient U-shaped member having an end wall; a pair of side walls extending perpendicular to said end wall apart for engaging said spring segment, and a prong extending from each said end wall for gripping said adjacent natural tooth, said end walls being formed so that when engaged with said spring segment, pressure on said gripping means in the direction of said offset sections will release said gripping means.

7. The dental restoration of claim 6, further comprising a base member located beneath said rigid bar and formed to rest on said ridge and between the natural teeth which define the edentulous space to be filled.

8. The dental restoration of claim 6 further comprising a plurality of restorations supported by said rigid bar.

9. The dental restoration of claim 6, further including a tool for releasing said gripping means, comprising: a removal bar having at each end a tip protruding at an angle to the longitudinal axis of said removal bar, said tips being spaced apart to contact simultaneously the end walls of said gripping means, whereby when said tips are in contact with said end walls, said gripping means may be released by pressing said removal bar toward said rigid bar.

10. A removable dental restoration for filling an edentulous space defined at least at one end by a natural tooth, comprising:
a central body portion shaped to simulate a natural tooth, the central body portion comprising a pair of substantially parallel, resilient longitudinal end walls and a pair of substantially rigid end walls joining to and substantially perpendicular to said longitudinal walls, said longitudinal and end walls forming a spring base member; and rigid means shaped to simulate the upper surface of a natural tooth for crowning said spring base member; and
gripping means extending from each said longitudinal wall for at least partially encircling and releasably gripping and adjacent natural tooth, whereby said gripping means resiliently clamps said restoration and can be released by applying pressure inwardly against said longitudinal walls, said substantially rigid end walls serving as fulcrum points about which said gripping means pivot for movement away from gripping engagement with said ajcent natural tooth when such inward pressure is applied.

11. The dental restoration of claim 10, wherein each said longitudinal wall includes means for receiving a corresponding gripping means, and said gripping means include means for mating with said receiving means, whereby each said gripping means is firmly retained on a longitudinal wall.

12. The dental restoration of claim 10, wherein said substantially rigid end walls comprise the side walls of an inserted U-shaped member having a base wall connecting the end walls, said crown means being secured to said base wall.

13. The dental restoration of claim 12, wherein said crown means is bonded to said base wall.

14. The dental restoration of claim 12, wherein said crown means includes means for engaging a securing means on said base wall and said base wall includes means complementary to said engaging means for securing said crown means to said base wall.

15. The dental restoration of claim 10, wherein said central body portion further comprises a resilient filler member formed to rest upon the ridge and tissue between the natural teeth which define the edentulous to be filled.

* * * * *